United States Patent [19]

Miyakawa et al.

[11] Patent Number: 5,866,355
[45] Date of Patent: Feb. 2, 1999

[54] DEVICE FOR MEASURING AN INTRACELLULAR ION CONCENTRATION

[75] Inventors: Atsuo Miyakawa; Masahiko Hirano; Kiyoshi Kamiya, all of Hamamatsu, Japan

[73] Assignees: Hamamatsu Photonics, K.K.; Atsuo Miyakawa, both of Hamamatsu, Japan

[21] Appl. No.: 656,826

[22] Filed: Jun. 3, 1996

Related U.S. Application Data

[60] Division of Ser. No. 309,317, Sep. 20, 1994, Pat. No. 5,550,031, which is a continuation-in-part of Ser. No. 110,173, Aug. 23, 1993, abandoned.

[30] Foreign Application Priority Data

Aug. 24, 1992 [JP] Japan ..................... 4-224151

[51] Int. Cl.$^6$ ..................... C12Q 1/02
[52] U.S. Cl. ............ 435/29; 435/288.7; 435/973; 436/74; 250/273
[58] Field of Search ............ 435/29, 968, 473, 435/287.1, 288.7; 436/63, 74, 172; 250/365, 372, 373, 458.1, 459.1, 461.1, 461.2

[56] References Cited

U.S. PATENT DOCUMENTS

| | | |
|---|---|---|
| 4,603,209 | 7/1986 | Tsien et al. . |
| 4,849,362 | 7/1989 | DeMarinis et al. . |
| 4,900,934 | 2/1990 | Peeters et al. . |
| 5,049,673 | 9/1991 | Tsien et al. . |
| 5,097,135 | 3/1992 | Makino et al. . |
| 5,149,972 | 9/1992 | Fay et al. . |
| 5,319,209 | 6/1994 | Miyakawa et al. . |
| 5,550,031 | 8/1996 | Miyakawa et al. ............ 435/29 |

FOREIGN PATENT DOCUMENTS

| | | |
|---|---|---|
| 4026564 | 2/1991 | Germany . |
| 4239016 | 5/1993 | Germany . |
| 381648 | 4/1991 | Japan . |

OTHER PUBLICATIONS

Nelder et al, "A simplex Method for Funcrion Minimization", Computer J., vol. 7, (1965) pp. 308–313.

Bancel et al, "investigation of Noncalcium Interactions of Fura–2 by classical and Synchronous Fluorescence Spectroscopy", Analytical Biochemistry 204, pp. 231–238 (1992).

Deeming et al, "Simplex Optimization of Variables in Analytical Chemistry", Analytical Chemistry, vol. 45, No. 3, Mar. 1973, pp. 278–282.

Lettanzio, "The effects of PH and Temperatureon Fluorescent Calcium Indicators as Determined with Chelex–100 and EDTA Buffer Systems", Biochemical and Biophysical Research Communications, vol. 171, No. 1, 1990, pp. 102–108.

Konishi et al, "Myoplasmic Binding of Fura–2 Investigated by Stedy–State Fluorescene and Absorbance Measurements", Biophysical Journal, vol. 54, 1988, pp. 1089–1988.

Grynkiewicz et al, "A New Generation of $Ca^{2+}$ Indicators with Greatly Improved Fluorescence Properties" [funded by NIH grants], The Journal of Biological Chemistry, 1985 vol. 260, No. 6, Mar. 25, pp. 3440–3450.

Miyakawa, "SI–3 Measurement of Intracellular Ion Concentration Using Fluorescent Probe Dyes", Photomedicine and Photobiology, vol. 13, 1991, pp. 15–18.

Miyakawa, "Determination of intracellular free calcium ion distribution with Fluorescent calcium reagent Fura–2 using video image processing" Biomedical Research Center Olympus Optical Co., Ltd. 2–3, Kuboyama–cho, Hachioii–shi, Tokyo 192 (Received Jul. 3, 1989); including one page English text of reprint from Bunseki Kagaku vol. 38, 1989 No. 11 pp. 643–649.

Partial English translation of the Magazine, "Analysis Jun. 1988", pp. 397–403.

*Primary Examiner*—Ralph Gitomer
*Attorney, Agent, or Firm*—Pillsbury Madison & Sutro, LLP; Intellectual Property Group

[57] ABSTRACT

A device for measuring an intracellular ion concentration in a living cell into which a fluorescent probe dye has been introduced. A concentration of an ion in the cell is measured based on intensities of fluorescence generated by irradiating the cell with excitation beams, and comparing the intensities of fluorescence emitted by the cell with fluorescence intensities generated from each of 3 reference solutions irradiated with excitation beams. The device is composed of a container means for holding an object to be measured, an excitation beam irradiating means, a fluorescence intensity detecting means, a first processing means for receiving output signals of the fluorescence intensity detecting means and a second processing means for solving simultaneous equations to determine a concentration of the ion to be measured within the cell.

24 Claims, 9 Drawing Sheets

Fig. 4

| Fig.4A |
|---|
| Fig.4B |

DEVICE FOR MEASURING AN INTRACELLULAR ION CONCENTRATION

RELATED APPLICATIONS

This is a division of application Ser. No. 08/309,317, filed Sep. 20, 1994, now U.S. Pat. No. 5,550,031 which is a Continuation-in-Part application of application Ser. No. 08/110,173, filed Aug. 23, 1993 now abandoned.

BACKGROUND OF THE INVENTION

1. Field of the Invention

The present invention relates to a method and a device for measuring distributions and changes of concentrations of intracellular ions which contribute to controls, etc. of cell functions.

2. Related Background Art

Fluorescent probe dyes, such as Fura-2, Indo-1, etc., are used to determine concentrations of ions, such as calcium ions, etc. present in live cells. Methods for synthesizing these dyes., and characteristics of these dyes are described in the following references, "The Journal of Biological Chemistry (1985), Vol. 260, p. 3340–3450" and "Biophysical Journal, Vol. 54, (1988), p. 1089–1104". These probe dyes have the property that their fluorescence characteristics change depending on bonds and dissociations of specific ions. To measure intracellular ion concentrations by using such property, the probe dyes are introduced into cells, and intensities of fluorescence generated by an excitation beam of certain wavelength are measured.

But the measurement based on an excitation beam at only one wavelength and fluorescence of only one wavelength cannot give accurate measured values when an concentration of probe dyes in the cell are unknown or a distribution of probe dyes in the cell is disuniform. There is a risk that changes of fluorescence intensities which do not depend on ion concentrations but caused by decreases of the fluorescence may be also measured.

As a method for removing this risk, fluorescence intensities for excitation beams of two different wavelengths, and intensities of fluorescence of two different wavelengths for one kind of an excitation beam are respectively measured, and their respective ratios are measured.

This method is described in good detail in Atsuo Miyakawa et al., "Bunseki Kagaku, Vol. 38, No. 11, p.642–p.649 (1989)", and "Photomedicine and Photobiology, Vol. 13, p.15–p.19 (1991)".

The above-described dual wavelength fluorescence measuring method is usable for systems to only a certain ion of which the probe dyes is reactive, but it is considered that the probe dyes bond with proteins and components other than ions, which are present in high concentrations in cells. Accordingly fluorescence emission spectra and chelate constants are adversely changed. This dual wavelength fluorescence measuring method cannot correct errors due to interactions between the dyes and components other than ions. Accurate ion concentrations cannot be determined.

SUMMARY OF THE INVENTION

An object of the present invention is to provide a method and a device for measuring an intracellular ion concentration which can decrease labor for preparing samples, and for measuring fluorescence intensities with high reliability.

A method for measuring an intracellular ion concentration according to the present invention, in which a fluorescence probe dye is introduced into a cell, and a concentration of ions to be measured in the cell is measured, based on intensities of fluorescence generated by irradiating the cell with excitation beams, comprises the first step of irradiating a first number of first type solutions of (1) the fluorescence probe dye and (2) the ions to be measured having different relative concentrations with either excitation beams at three different wavelengths or an excitation beam of one wavelength, measuring intensities of fluorescence generated by the excitation beams corresponding to the respective three wavelengths and the first number of the first type solutions, or measuring intensities of the fluorescence of three wavelengths generated by the excitation beam corresponding to the respective first number of the first type solutions of the different relative concentrations;

the second step of irradiating a second number of second type solutions of (1) an interfering biosubstance which is a different substance from the ion to be measured, bonds with the fluorescent probe dye and the ion to be measured wherein the probe dye(s) bond with proteins and components other that ions, which are present in high concentrations in cells, and thereby changes a fluorescence intensity, and (2) the fluorescent probe dye with either excitation beams at three different wavelengths or an excitation beam of one wavelength, the second number of the second type solutions having different relative concentrations, measuring intensities of fluorescence generated by the excitation beams corresponding to the respective three different wavelengths and the second number of the second type solutions, or measuring intensities of fluorescence of three wavelengths generated by the excitation beam corresponding to the respective second number of the second type solutions of the different relative concentrations;

the third step of irradiating a third number of third type solutions of (1) the interfering biosubstance, (2) the fluorescent probe dye, and (3) the ions to be measured with either excitation beams at three different wavelengths or an excitation beam of one wavelength, the third number of the third type solutions having different relative concentrations, measuring intensities of fluorescence generated by the excitation beams corresponding to the respective three wavelengths and the third number of the third type solutions or measuring intensities of fluorescence of three wavelengths generated by the excitation beam corresponding to the respective second number of the second type solutions of the different relative concentrations;

the fourth step of, in accordance with a predetermined method of successive approximation, (1) setting initial values of three kinds of equilibrium constants: $K_{FI}$, $K_{PF}$ and $K_{PFI}$ in the following three kinds of independent equilibrium constant equations of the fluorescent probe dye, the ions to be measured, the interfering biosubstance and their complexes in the cell, and initial values of 12 kinds of fluorescence coefficients: $I_{\lambda 1,F}$, $I_{\lambda 2,F}$, $I_{\lambda 3,F}$, $I_{\lambda 1,PF}$, $I_{\lambda 2,PF}$, $I_{\lambda 3,PF}$, $I_{\lambda 1,FI}$, $I_{\lambda 2,FI}$, $I_{\lambda 3,FI}$, $I_{\lambda 1,PFI}$, $I_{\lambda 2,PFI}$, and $I_{\lambda 3,PFI}$ in the following relationship equations between the intensities of the fluorescence, and the concentrations of fluorescent probe dye, ions to be measured, interfering biosubstance, and their complexes, (2) calculating and comparing errors between fluorescence intensities calculated based on the initial values, and fluorescence intensities measured in the first to third steps, (3) if the error being within an allowable range, the three kinds of equilibrium constants and the 12 kinds of fluorescence coefficients being optimized, if the error exceeding the allowable range, setting new values of the three kinds of equilibrium constants and the 12 kinds of fluorescence coefficients, (4) calculating errors between calculated fluorescence intensities, and fluorescence intensities measured in the first to third steps, (5) comparing the error of this time with the previous error, and (6) if the error of this time being larger or equal to the previous error, or zero, the three kinds of equilibrium constants and the 12 kinds of fluorescence coefficients being optimized, if the error being less than the previous error but not zero, successively repeating setting new values of the three kinds of equilibrium constants and the 12 kinds of fluorescence coefficients, calculating errors between calculated fluorescence intensities, and fluorescence intensities measured in-the first to third steps and comparing the error of this time with the previous error until the error is larger or equal to the previous error, or zero;

the fifth step of either irradiating the cell with excitation beams at three different wavelengths and measuring intensities of the fluorescence generated by the excitation beams corresponding to the respective three different wavelengths, or irradiating the cell with an excitation beam of one wavelength and measuring intensities of the fluorescence of three wavelengths generated by the excitation beam; and the sixth step of solving simultaneous equations of (1) equilibrium constant equations of the fluorescence probe dye, protein, the ions to be measured and their complexes in the cell, and (2) relationship equations between the intensities of the fluorescence generated by the excitation beams at the respective wavelengths, and the concentrations of fluorescence probe dye, protein, the ions to be measured and their complexes, wherein the equations are $$K_{FI} = X_F \cdot X_I / X_{FI}$$

$$K_{PF} = X_P \cdot X_F / X_{PF}$$

$$K_{PFI} = X_P \cdot X_{FI} / X_{PFI} \text{ (or, } K_{PFI} = X_{PF} \cdot X_I / X_{PFI})$$

$$I_{\lambda 1} = I_{\lambda 1,F} \cdot X_F + I_{\lambda 1,PF} \cdot X_{PF} + I_{\lambda 1,FI} \cdot X_{FI} + I_{\lambda 1,PFI} \cdot X_{PFI}$$

$$I_{\lambda 2} = I_{\lambda 2,F} \cdot X_F + I_{\lambda 2,PF} \cdot X_{PF} + I_{\lambda 2,FI} \cdot X_{FI} + I_{\lambda 2,PFI} \cdot X_{PFI}$$

$$I_{\lambda 3} = I_{\lambda 3,F} \cdot X_F + I_{\lambda 3,PF} \cdot X_{PF} + I_{\lambda 3,FI} \cdot X_{FI} + I_{\lambda 3,PFI} \cdot X_{PFI}$$

wherein $X_F$: a concentration of a fluorescence probe dye, $X_I$: a concentration of ions to be measured $X_P$: a concentration of protein $X_{FI}$: a concentration of fluorescence probe dye-ions to be measured complexes $X_{PF}$: a concentration of protein-fluorescence probe dye complexes $X_{PFI}$: a concentration of protein-fluorescence probe dye-ions to be measured complexes $K_{FI}$: an equilibrium constant between fluorescence probe dye and ions to be measured $K_{PF}$: an equilibrium constant between protein and fluorescence probe dye $K_{PFI}$: an equilibrium constant among protein, fluorescence probe dye and ions to be measured $I_{\lambda i}$: a measured fluorescence intensity for an excitation beam of wavelength $\lambda_i$ $I_{\lambda i,F}$: a fluorescence intensity coefficient of a fluorescence probe dye for an excitation beam of wavelength $\lambda_i$ $I_{\lambda i,PF}$: a fluorescence intensity coefficient of protein-fluorescence probe dye complexes for an excitation beam of wavelength $\lambda_i$ $I_{\lambda i,FI}$: a fluorescence intensity coefficient of fluorescence probe dye-ions to be measured complexes for an excitation beam at wavelength $\lambda_i$ $I_{\lambda i,PFI}$: a fluorescence intensity coefficient of protein-fluorescence probe dye-ions to be measured complexes for excitation beam of a wavelength $\lambda_i$ i: 1, 2, 3.

It is preferable that the first number is four or more, the second number is three or more, and the third number is three or more.

The predetermined method of successive approximation can be a modified simplex method. In this case, 16 sets of the three kinds of equilibrium constants, and 16 sets of the initial values of the 12 kinds of fluorescence coefficients are set in the fourth step. Another method of successive approximation is, Jacobi method, a steepest descent method, a Gauss-Newton method, a Benet method etc.

The ions to be measured are, for example, $Ca^{2+}$, $Na^+$, $H^+$, $Mg^{2+}$ or others. The interfering biosubstance is, for example, bioprotein or others.

In the first, second, third and fifth steps, in the case that the excitation beams at three wavelengths are used and the fluorescence intensities generated by the excitation beams, corresponding to the respective three different wavelengths are measured (hereinafter called "three-wavelength excitation one-wavelength fluorescence measuring method), the fluorescence probe dye of Fura-2 is preferably used to $Ca^{2+}$, Sodium-binding benzofuran isophthalate to $Na^+$, 2',7'-bis-(2-carboxyethyl)-(5-(and-6)-carboxyfluoresoein) and carboxy-seminaphthorhodafluor-6 to $H^+$, and Mag-Fura-2 to $Mg^{2+}$ because of their fluorescence characteristics.

On the other hand, in the case that the excitation beam of one wavelength is used and the fluorescence intensities generated by the excitation beam of one wavelength are measured (hereinafter called "one wavelength excitation three-wavelength fluorescence measuring method), the fluorescence probe dye of Indo-1 is preferably used to $Ca^{2+}$, FCryp-2 to $Na^+$, Carboxyseminaphthorhodaflor-1 to $H^+$, Carboxyseminaphthorhodafluor-2 to $H^+$, Carboxyseminaphthorhodafluor-6 to $H^+$, Carboxyseminaphthorhodafluor-X to $H^+$, and Mag-indo-1 to $Mg^{2+}$.

The method of the above-described fifth step and sixth step for measuring fluorescence intensities for excitation beams of three different wavelengths, and the method for measuring intensities of fluorescence of three different wavelengths for an excitation beam of one wavelength (hereinafter called "three-wavelength fluorescence measuring method") are described in U.S. Pat. No. 5,319,209 titled "A method for measuring an intracellular ion concentration using fluorescent probe dyes".

This three-wavelength fluorescence measuring method will be explained by means of an example in which $Ca^{2+}$ is measured using Fura-2 is used as a fluorescent probe dye. Here an interfering biosubstance is represented by protein.

FIG. 1 is a view approximating interactions in a cell between Fura-2, and calcium ion ($Ca^{2+}$) or protein. In FIG. 1 shows a case in which $Ca^{2+}$ is measured using Fura-2, but a case where $Ca^{2+}$ is measured using, e.g., Indo-1 can be similarly approximated. In a cell Fura-2 bonds with $Ca^{2+}$ at an equilibrium constant K(FC) and also with protein at an equilibrium constant K(PF). Furthermore, three components, Fura-2, $Ca^{2+}$ and protein, are bonded at an equilibrium constant K(PFC) or K'(PFC). Accordingly, the following equations (1) to (4) hold on these three bonding components.

$$K(FC)=[F][C]/[FC] \quad (1)$$

$$K(PF)=[P][F]/[PF] \quad (2)$$

$$K(PFC)=[P][FC]/[PFC] \quad (3)$$

$$K'(PFC)=[PF][C]/[PFC] \quad (4)$$

In the above-described equations, F represents Fura-2; C, $Ca^{2+}$; P, protein; and [ ], a concentration of a component.

Then excitation beams irradiate the above-described samples, and spectra of the generated fluorescence are measured. The excitation beams have three wavelengths of 340 nm, 360 nm and 380 nm. Since four components, Fura-2, Fura-2-calcium ion complex, Fura-2-protein complex, Fura-2-calcium ion-protein complex, are present in a cell, an intensity of the fluorescence corresponding to each wavelength is a sum of intensities of the fluorescence of the respective components. Accordingly the following equations (5) to (7) hold.

$$I_{340}=[F]I(F)_{340}+[PF]I(PF)_{340}+[FC]I(FC)_{340}+[PFC]I(PFC)_{340} \quad (5)$$

$$I_{360}=[F]I(F)_{360}+[PF]I(PF)_{360}+[FC]I(FC)_{360}+[PFC]I(PFC)_{360} \quad (6)$$

$$I_{380}=[F]I(F)_{380}+[PF]I(PF)_{380}+[FC]I(FC)_{380}+[PFC]I(PFC)_{380} \quad (7)$$

In these equations, an equilibrium constant K(FC) between Fura-2 and $Ca^{2+}$, an equilibrium constant (PF) between Fura-2 and protein, an equilibrium constant K(PFC) between Fura-2-calcium ion complex and protein, an equilibrium constant K'(PFC) between Fura-2-protein complex, and calcium ion, fluorescence intensities I(F) of Fura-2 at a 340 nm-, 360 nm- and 380 nm-wavelengths, a fluorescence intensity I(FC) of Fura-2-calcium ion complex, a fluorescence-intensity I(PF) of Fura-2-protein complex, and a fluorescence intensity I(PFC) of Fura-2-calcium ion -protein complex are known values.

Accordingly, respective fluorescence intensities $I_{340}$, $I_{360}$, $I_{380}$ of a cell with Fura-2 introduced into, at 340 nm-, 360-nm and 380-nm-wavelengths of the excitation beams are measured, and simultaneous equations (1) to (7) are solved, whereby an intracellular ion $Ca^{2+}$ concentration can be obtained.

In this method, as described above, it is necessary to calculate an ion concentration that the following 15 kinds of constants must be preset:

Light absorption coefficients or fluorescence coefficients (three kinds) at three different wavelengths to be used in measuring a probe dye;

Light absorption coefficients or fluorescence coefficients (three kinds) at the three different wavelengths to be used in measuring the probe dye—an ion complex;

Light absorption coefficients or fluorescence coefficients (three kinds) at the three wavelengths to be used in measuring interfering biosubstance—the probe dye complex;

Light absorption coefficients or fluorescence coefficients (three kinds) at the three wavelengths to be used in measuring the interfering biosubstance—the probe dye—the ion complex;

An equilibrium constant (one kind) between the probe dye and the ion;

An equilibrium constant (one kind) between the interfering biosubstance—the probe dye; and An equilibrium constant (one kind) between the interfering biosubstance and the probe dye—the ion complex, or an equilibrium constant (one kind) between the interfering biosubstance—the probe dye complex and the ion (when one is obtained, the other can be calculated. Empirically the former is convenient.)

These 15 constants are obtained by the above-described first to the fourth steps. These constants are obtained by a method of successive approximation, e.g., a modified simplex method. The modified simplex method is described in good detail in Kawaguchi, "Optimization by Simplex Method", Analysis, June, 1988, pp. 397–403", and "J. A. Nelder, R. Mead: Computer J., 7, 308 (1965)".

FIG. 2 shows the relationships between concentrations of solutions of Fura-2 as a fluorescent probe dye, $Ca^{2+}$ as an ion to be measured and protein as an interfering biosubstance, and fluorescence intensities. In the part (a) of FIG. 2, fluorescence intensities at the respective excitation-wavelengths are measured with contents of the protein of solutions of Fura-2 and protein changed.

In the part (b) of FIG. 2, fluorescence intensities at the respective excitation wavelengths are measured with contents of the $Ca^{2+}$ of solutions of Fura-2 and $Ca^{2+}$ changed. In the-part (c) of FIG. 2, fluorescence intensities at the respective excitation wavelengths are measured with contents of the protein of solutions of complexes of Fura-2 and $Ca^{2+}$, and the protein changed.

In the part (b) of FIG. 2, fluorescence intensities at the respective wavelengths of the excitation beams theoretically agree with one another (the lines corresponding to the respective excitation beam wavelengths intersect one another at one point) at a specific $Ca^{2+}$ concentration. At this point a concentration value of the $Ca^{2+}$ agrees with an equilibrium constant between Fura-2 and the $Ca^{2+}$. Similarly in the part (a) of FIG. 2, the lines corresponding to the respective excitation beam wavelengths intersect one another at one point, where a protein concentration value agrees with an equilibrium constant between Fura-2 and the protein. Also in the part (c) of FIG. 3, the lines corresponding to the respective excitation beam wavelengths intersect one another at one point, where a protein concentration value agrees with an equilibrium constant between Fura-2, the $Ca^{2+}$ and the protein.

In the above-described method, the solutions of a fluorescent probe dye and ions to be measured, having four or more different concentrations are used. This is because, as shown in the part (b) of FIG. 2, fluorescence intensities are measured at totally four points where the ion ($Ca^{2+}$) concentration is respectively lower and higher, and two points between the lower and higher points, whereby equilibrium constants can be obtained by the method of the present invention. Further, solutions of the fluorescent probe dye and an interfering biosubstance having three or more different concentrations are used. This is because, as shown in the part (a) of FIG. 2, a higher point where the interfering biosubstance (protein) has a higher concentration has the same value as at a lower point where the ion ($Ca^{2+}$) concentration is lower in the part (b) of FIG. 2, so that three kinds of solutions which are one kind smaller compared with the solutions of a fluorescent probe dye and an ion to be measured are used. Furthermore, solutions of the fluorescent probe dye, the ion and the interfering biosubstance having three or more different concentrations are used. This is because, as shown in the part (C) of FIG. 2, a lower point where the interfering biosubstance (protein) has a lower concentration has the same value as at a higher point where the ion ($Ca^{2+}$) concentration is higher in the part (b) of FIG. 2.

Thus, in the method for measuring an intracellular ion concentration according to the present invention, the constants are not given by analytically solving a higher order equation, but are given by a method of successive approximation, whose calculation can be easily programmed. The use of a computer can improve the efficiency of determining the constants. Furthermore, what has to be done to determine the constants is to prepare tens of kinds of samples, and measure fluorescence intensities, which can drastically decrease the labor of preparation of samples and fluorescence intensity measurement. Furthermore, since an intracellular ion concentration is given based on thus reliably given constants, the resultant ion concentration can be more accurate.

Next, the device for measuring an intracellular ion concentration, which is used in the above-described method according to the present invention will be explained below.

A device for measuring an intracellular ion concentration according to a first aspect of the present invention, which is used for the three-wavelength excitation one-wavelength fluorescence measuring method, comprises a container for holding an object to be measured, the object to be measured being one of a cell with a fluorescent probe dye introduced in, and a plurality of different type solutions of the fluorescent probe dye to be used to quantize a concentration of ions to be measured, the ions to be measured, an interfering biosubstance which is a different substance from the ion to be measured, bonds with the fluorescent probe dye and the ion to be measured and thereby changes a fluorescence intensity, and their complexes;

excitation beam irradiating means for generating excitation beams of three different wavelengths and irradiating the object to be measured in the container with the excitation beams at three different wavelengths;

fluorescence intensity detecting means for measuring intensities of fluorescence generated by the excitation beams;

first processing means for receiving output signals of the fluorescence intensity detecting means, storing the output signals, and in accordance with a predetermined method of successive approximation, using the output signals stored, optimizing three kinds of equilibrium constants: $K_{FI}$, $K_{PF}$ and $K_{PFI}$ in the following three kinds of independent equilibrium constant equations of the fluorescent probe dye, the ions to be measured, the interfering biosubstance and their complexes in the cell, and 12 kinds of fluorescence coefficients: $I_{\lambda 1,F}$, $I_{\lambda 2,F}$, $I_{\lambda 3,F}$, $I_{\lambda 1,PF}$, $I_{\lambda 2,PF}$, $I_{\lambda 3,PF}$, $I_{\lambda 1,FI}$, $I_{\lambda 2,FI}$, $I_{\lambda 3,FI}$, $I_{\lambda 1,PFI}$, $I_{\lambda 2,PFI}$, and $I_{\lambda 3,PFI}$ in the following relationship equations between the intensities of the fluorescence, and the concentrations of fluorescent probe dye, ions to be measured, interfering biosubstance, and their complexes by (1) setting initial values of the three kinds of equilibrium constants, and initial values of the 12 kinds of fluorescence coefficients,: (2) calculating and comparing errors between fluorescence intensities calculated based on the initial values, and fluorescence intensities measured in the first to third steps, (3) if the error being within an allowable range, the three kinds of equilibrium constants and the 12 kinds of fluorescence coefficients being optimized, if the error exceeding the allowable range, setting new values of the three kinds of equilibrium constants and the 12 kinds of fluorescence coefficients, (4) calculating errors between calculated fluorescence intensities, and fluorescence intensities measured in the first to third steps, (5) comparing the error of this time with the previous error, and (6) if the error of this time being larger or equal to the previous error, or zero, the three kinds of equilibrium constants and the 12 kinds of fluorescence coefficients being optimized, if the error being less than the previous error but not zero, successively repeating setting new values of the three kinds of equilibrium constants and the 12 kinds of fluorescence coefficients, calculating errors between calculated fluorescence intensities, and fluorescence intensities measured in the first to third steps and comparing the error of this time with the previous error until the error is larger or equal to the previous error, or zero; and second processing means for determining a concentration of the ions to be measured in the cell by solving simultaneous equations of (1) equilibrium constant equations of the fluorescence probe dye, protein, the ions to be measured and their complexes in the cell, and (2) relationship equations between the intensities of the fluorescence generated by the excitation beams at the respective wavelengths, and the concentrations of fluorescence probe dye, protein, the ions to be measured and their complexes, wherein the equations are $K_{FI} = X_F \cdot X_I / X_{FI}$ $K_{PF} = X_P \cdot X_F / X_{PF}$ $K_{PFI} = X_P \cdot X_{FI} / X_{PFI}$ (or, $K_{PFI} = X_{PF} \cdot X_I / X_{PFI}$)

$I_{\lambda 1} = I_{1\lambda 1,F} \cdot X_F + I_{\lambda 1,PF} \cdot X_{PF} + I_{\lambda 1,FI} \cdot X_{FI} + I_{\lambda 1,PFI} \cdot X_{PFI}$ $I_{\lambda 2} = I_{\lambda 2,F} \cdot X_F + I_{\lambda 2,PF} \cdot X_{PF} + I_{\lambda 2,FI} \cdot X_{FI} + I_{\lambda 2,PFI} \cdot X_{PFI}$ $I_{\lambda 3} = I_{\lambda 3,F} \cdot X_F + I_{\lambda 3,PF} \cdot X_{PF} + I_{\lambda 3,FI} \cdot X_{FI} + I_{3,PFI} \cdot X_{PFI}$ wherein $X_F$: a concentration-of a fluorescence probe dye, $X_I$: a concentration of ions to be measured $X_P$: a concentration of protein $X_{FI}$: a concentration of fluorescence probe dye-ions to be measured complexes $X_{PF}$: a concentration of protein-fluorescence probe dye complexes $X_{PFI}$: a concentration of protein-fluorescence probe dye-ions to be measured complexes $K_{FI}$: an equilibrium constant between fluorescence probe dye and ions to be measured $K_{PF}$: an equilibrium constant between protein and fluorescence probe dye $K_{PFI}$: an equilibrium constant among protein, fluorescence probe dye and ions to be measured $I_{\lambda i}$: a measured fluorescence intensity for an excitation beam of wavelength $\lambda_i$ $I_{\lambda i,F}$: a fluorescence intensity coefficient of a fluorescence probe dye for an excitation beam of wavelength $\lambda_i$ $I_{\lambda i,PF}$: a fluorescence intensity coefficient of protein-fluorescence probe dye complexes for an excitation beam of wavelength $\lambda_i$ $I_{\lambda i,FI}$: a fluorescence intensity coefficient of fluorescence probe dye-ions to be measured complexes for an excitation beam at wavelength $\lambda_i$ $I_{\lambda i, PFi}$: a fluorescence intensity coefficient of protein-fluorescence probe dye-ions to be measured complexes for excitation beam of a wavelength $\lambda_i$ i: 1, 2, 3.

The excitation beam irradiating means can comprise one light source for emitting beams of a wavelength range including three wavelengths of the excitation beams to be used, and three filters through which a beam of a wavelength range near the respective wavelength of the excitation beam passes. One of the three filters are selected in accordance with the predetermined wavelength of the excitation beam, and the beam of the predetermined wavelength near the wavelength of the excitation beam passes through the selected filter.

Alternatively, the excitation beam irradiating means can comprise three light sources for emitting an excitation beam of a different wavelength. One of the light sources is selected in accordance with the predetermined wavelength of the excitation beam, and the excitation beam of the predetermined wavelength is emitted from the selected light source.

The predetermined method of successive approximation can be a modified simples method. In this case, 16 sets of the values of the three kinds of equilibrium constants and the 12 fluorescence coefficients are set in the first processing means in accordance with the modified simplex method.

The ions to be measured are, for example, $Ca^{2+}$, $Na^+$, $H^+$, $Mg^{2+}$ or others. The interfering biosubstance is, for example, bioprotein or others.

The fluorescence probe dye of Fura-2 is preferably used to $Ca^{2+}$, Sodium-binding benzofuran isophthalate to $Na^{30}$, 2',7'-bis-(2-carboxyethyl)-(5-(and-6)-carboxyfluoresoein) and carboxy-seminaphthorhodafluor-6 to $H^+$, and Mag-Fura-2 to $Mg^{2+}$ because of their fluorescence characteristics.

A device for measuring an intracellular ion concentration according to a second aspect of the present invention is used for the above-described one-wavelength three-wavelength fluorescence measuring method and comprises a container, excitation beam irradiating means, fluorescence intensity detecting means, first processing means and second processing means. The container, the first processing means and the second processing means are the same as those of the first aspect of the present invention. Here will be explained excitation beam irradiating means and the fluorescence intensity detecting means which are different from those of the first embodiment.

Excitation beam irradiating means generates an excitation beam of one wavelength and irradiates the object to be measured in the container with the excitation beam.

Fluorescence intensity detecting means measures intensities of fluorescence generated by the excitation beams of three wavelengths.

The excitation beam irradiating means can comprise one light source for emitting beams of a wavelength range including one wavelength of the excitation beam to be used, and one filter through which a beam of a wavelength range near the wavelength of the excitation beam to be used passes.

Alternatively, the excitation beam irradiating means can comprise a light source for emitting the excitation beam of one wavelength.

The fluorescence intensity detecting means can comprise three filters through which fluorescence light of different wavelength ranges passes. One of the three filters is selected in accordance with a predetermined fluorescence wavelength range, and fluorescence of the predetermined fluorescence wavelength range passes through the selected filter.

Here, the fluorescence probe dye of Indo-1 is preferably used to $Ca^{2+}$, FCryp-2 to $Na^+$, Carboxyseminaphthorhodaflor-1 to $H^+$,
Carboxyseminaphthorhodafluor-2 to $H^+$,
Carboxyseminaphthorhodafluor-6 to $H^+$,
Carboxyseminaphthorhodafluor-X to $H^+$, and Mag-indo-1 to $Mg^{2+}$.

Thus, in the device for measuring an intracellular ion concentration according to the present invention, constants are given by a method of successive approximation. Accordingly given constants can be highly reliable. Intracellular ion concentrations measured based on such highly reliable constants can be accurate.

The method and the device for measuring an intracellular ion concentration of the present invention can be applied to intracellular ions and fluorescence probe dyes incorporated in U.S. Pat. No. 5,319,209.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art form this detailed description.

BRIEF DESCRIPTION OF THE DRAWINGS

FIG. 2a relates shifts in fluorescence intensity with varying protein concentrations. FIG. 2b relates changes in fluorescence with varying concentration of $Ca^{2+}$. FIG. 2c relates changes in fluorescence with varying protein concentration and a fixed concentration of $Ca^{2+}$.

FIG. 4 shows a relationship between FIG. 4A and FIG. 4B.

DESCRIPTION OF PREFERRED EMBODIMENTS

Embodiments of the present invention will be explained with reference to the drawings.

In a method and device for measuring an intracellular ion concentration according to a first embodiment, Fura-2 is used as a fluorescent probe dye, and objects to be measured are irradiated with excitation beams at three different wavelengths, and fluorescence intensities generated by the excitation beams corresponding to three different wavelengths are measured to determine a $Ca^{2+}$ concentration. Further, a modified simplex method is used as a method of successive approximation.

Figure 1:
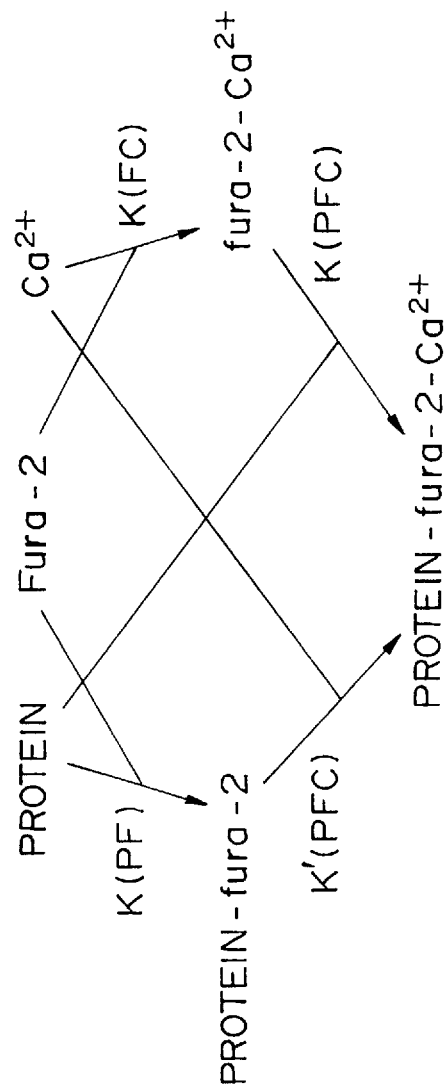
FIG. 1 is a view of interactions between Fura-2 and protein.
Figure 2:
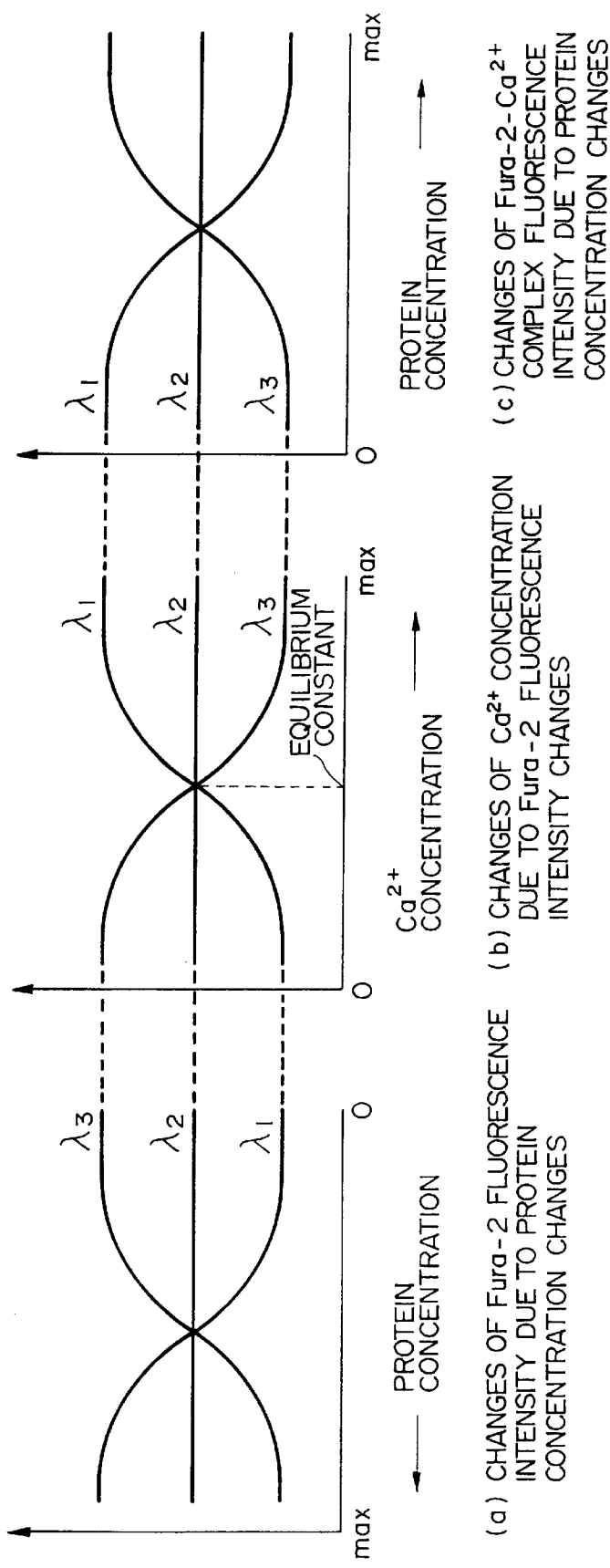
FIG. 2 is a view of interrelationships between fluorescence intensities and concentrations of Fura-2, protein, $Ca^{2+}$ and their complex.
Figure 3:
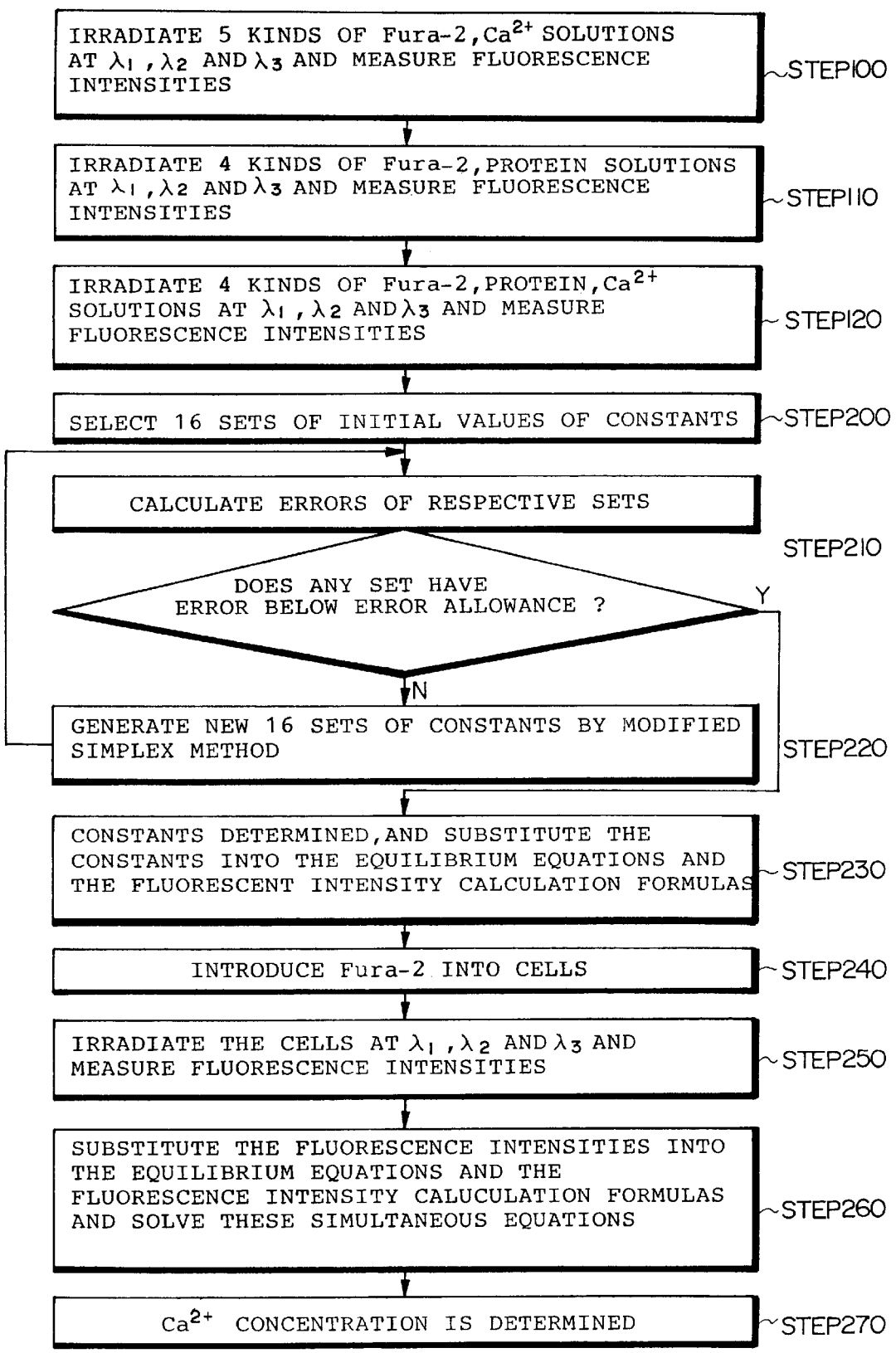
FIG. 3 is a flow chart of the method for measuring an intracellular ion concentration according to a first embodiment of the present invention, where Fura-2 is used.

First, a method according to the first embodiment will be explained. FIG. 3 shows the flow chart of the method of the first embodiment.

Five kinds of solutions of Fura-2 and $Ca^{2+}$ having different concentrations are prepared. The five kinds of solutions are irradiated with excitation beams at three different wavelengths of $\lambda_1=340$ nm, $\lambda_2=360$ nm and $\lambda_3=380$ nm, and fluorescence intensities generated by the excitation beams corresponding to the respective wavelengths and five kinds of solutions are measured (Step 100 in FIG. 3). Next, four kinds of solutions of Fura-2 and protein having different concentrations are prepared. The four kinds of solutions are irradiated with excitation beams at three different wavelengths of $\lambda_1=340$ nm, $\lambda_2=360$ nm and $\lambda_3=380$ nm, and fluorescence intensities generated by the excitation beams corresponding to the respective wavelengths and five kinds of solutions are measured (Step 110 in FIG. 3). Four kinds of solutions of Fura-2, protein and $Ca^{2+}$ having different concentrations are prepared. The four kinds of solutions are irradiated with excitation beams at three different wavelengths of $\lambda_1=340$ nm, $\lambda_2=360$ nm and $\lambda_3=380$ nm, and fluorescence intensities generated by the excitation beams corresponding to the respective wavelengths and five kinds of solutions are measured (Step 120 in FIG. 3).

Subsequently, in accordance with the modified simplex method, 16 sets of initial values of fluorescence coefficients ([F], [PF], [FC] and [PFC] in equations (5), (6) and (7)) and of equilibrium constants (K(FC), K(PF), K(PFC) or K'(PFC) in equations (1), (2), (3) and (4)) are arbitrary set (Step 200 in FIG. 3). Initial values of the respective constants are selected so as not to be physically insignificant solutions because the respective constants are synthetically ones of solutions of cubic equations. Based on dispersions of measured fluorescence intensity against the fluorescence intensity calculating equations (relationship equations (5), (6) and (7)) with the respective sets of initial values, errors are calculated, and it is judged whether there are sets whose errors are in an allowable error range (Step 210 in FIG. 3). If present, one of such sets having a smallest error is judged to be an optimum set of the constants (Step 230 in FIG. 3). If absent, a new set is calculated in accordance with the modified simplex method, based on a set having the largest error, a set having the next largest error and a set having the smallest error, and this new set is replaced with the set having the largest error to generate new 16 sets of the constants (Step 220 in FIG. 3). Subsequently Step 210 follows, and Steps 210 and 220 are repeated until a set with an error within the allowable error range appears.

Here, referring to FIGS. 4, 4A and 4B, the procedure of steps 200, 210 and 220 will be explained in detail.

Figure 4A:
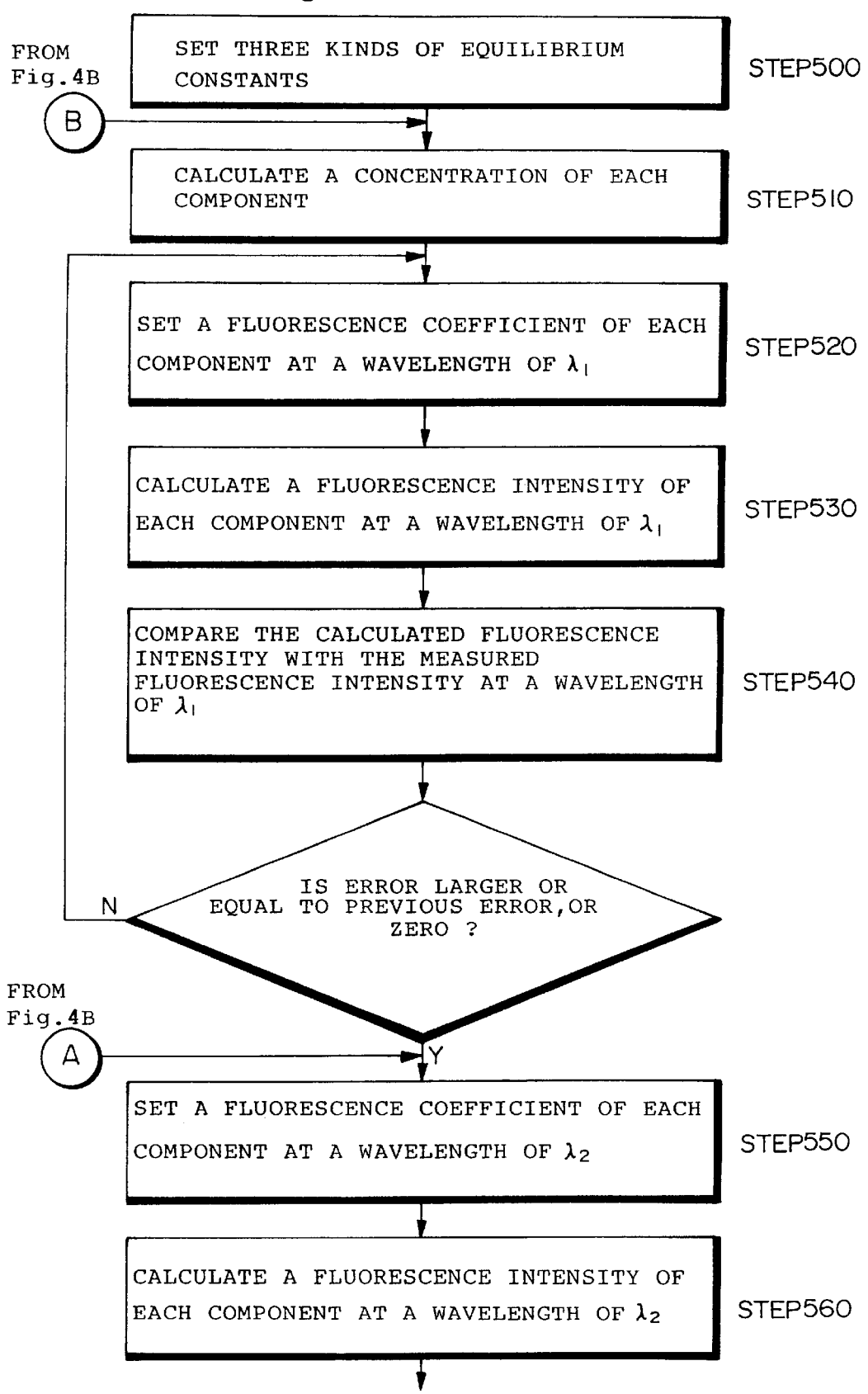
FIGS. 4A and 4B are flow charts of steps 200, 210 and 220 shown in FIG. 3.

First, three kinds of equilibrium constants are set (Step 500 in FIG. 4A), and a concentration of each component is calculated (Step 510 in FIG. 4A). Next, 16 sets of fluorescence coefficients of components at a wavelength of $\lambda_1$ (see equation (5)) are set (Step 520 in FIG. 4A), and a fluorescence intensity of each component at a wavelength of $\lambda_1$ is calculated (Step 530 in FIG. 4A). Each set of the calculated fluorescence intensity is compared with the measured fluorescence intensity and errors are calculated (Step 540). If there are sets the errors of which are in an allowable range, the set having the smallest error is judged to be an optimum set of the constants, and the process proceeds to Step 550. If not, the process goes back to Step 520 and a new set is calculated based on the set with the largest error, the set having the next largest error and the set having the smallest error in accordance with the simplified method, and this new set is replaced with the set having the largest error. Each set of the calculated fluorescence intensity is compared with the measured fluorescence intensity (Step 540) and errors are calculated. If the difference between the largest error and the smallest error is larger or equal to the previous difference, or zero, the smallest error set is judged to be an optimum set and the process proceeds to Step 550. If the difference between the largest error and the smallest error is smaller than the previous difference but not zero, Steps 520, 530 and 540 are repeated until the difference is larger or equal to the previous error, or zero. The same procedure is conducted for wavelengths $\lambda_2$ and $\lambda_3$ (Steps 550–600). Then, at this point, 12 kinds of fluorescence coefficients and three kinds of equilibrium constants are optimized. Then, the summation of the calculated intensities at $\lambda_1$, $\lambda_2$, and $\lambda_3$ is compared with the summation of the measured intensities at $\lambda_1$, $\lambda_2$ and $\lambda_3$. If the error between the calculated one and the measured one is within an allowable range, the fluorescence coefficients and the equilibrium constants are determined. If the error is not within an allowable range, the process goes back to Step 500, and repeats Steps 500–610 until the error between the summation of the measured intensities at $\lambda_1$, $\lambda_2$ and $\lambda_3$ and the summation of the calculated intensities at $\lambda_1$, $\lambda_2$ and $\lambda_3$ is within an allowable range.

As described above, 15 kinds of constants are optimized to determine respective highly reliable fluorescence coefficients and equilibrium constants (Step 230 in FIG. 3).

Then Fura-2 is introduced into a cell (Step 240 in FIG. 3). The cell is irradiated with the excitation beams at the above-described three different wavelengths. Fluorescence intensities generated by excitation beams at the three wavelengths are measured (Step 250 in FIG. 3). These measured fluorescence intensities are substituted in the equilibrium constant equations and the fluorescence intensity calculating equations (relationship equations) and these simultaneous equations are solved (Step 260 in FIG. 3), and then the $Ca^{2+}$ concentration is obtained (Step 270 in FIG. 3).

Thus, as described above, an intracellular ion concentration can be measured with high reliability.

In the first embodiment, a fluorescent probe dye is provided by Fura-2, but when other probe dyes, e.g., Indo-1, is used as a fluorescent probe dye, it is preferred because of the fluorescence characteristics of Indo-1 that the one-wavelength excitation three-wavelength fluorescence measurement is conducted.

Figure 5:
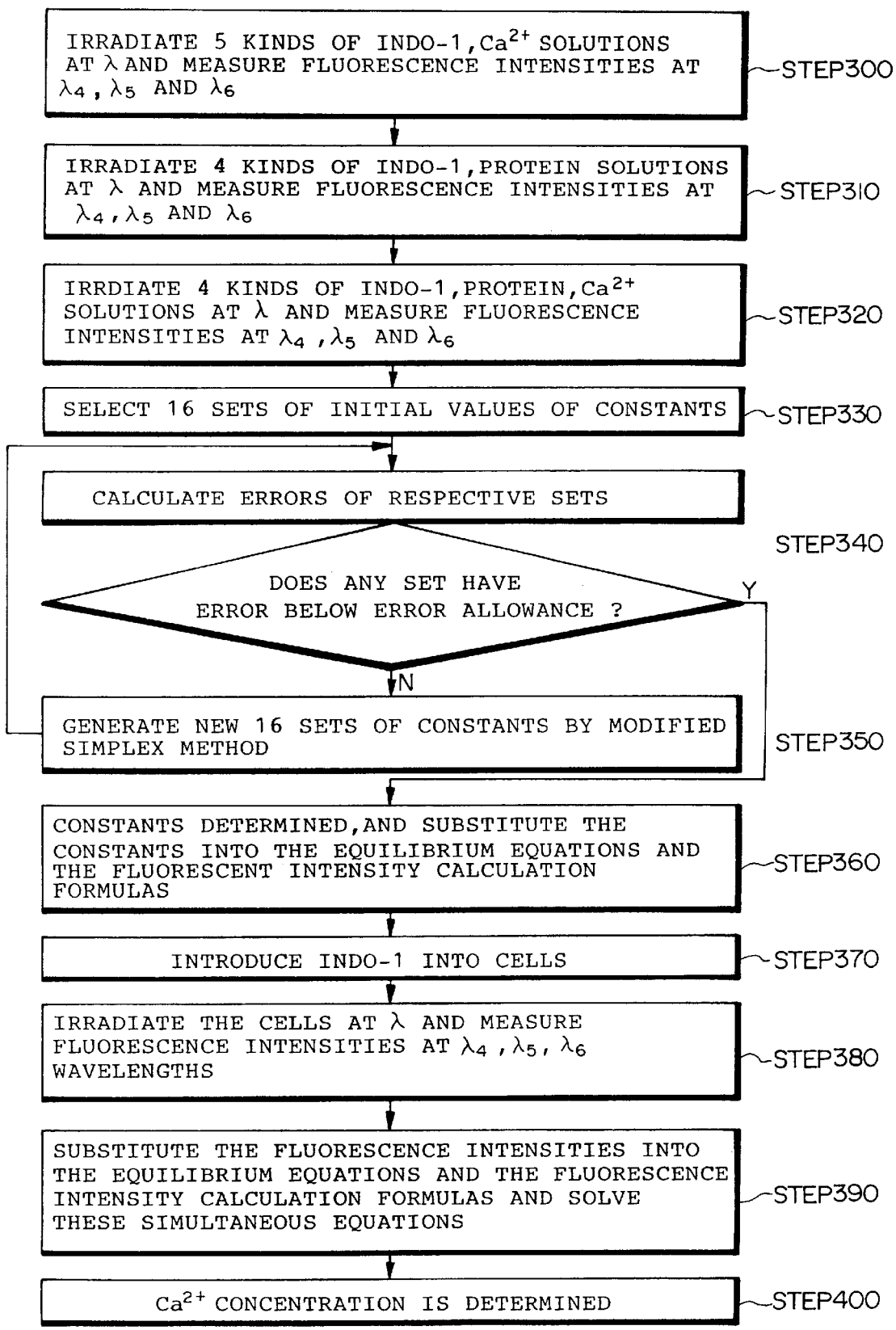
FIG. 5 is a flow chart of the method for measuring an intracellular ion concentration according to a second embodiment of the present invention, where Indo-1 is used.

FIG. 5 is a flow chart of the method for measuring an intracellular ion concentration according to a second embodiment of the present invention, in which a fluorescent probe dye is provided by Indo-1.

Five kinds of solutions of Indo-1 and $Ca^{2+}$ having different concentrations are prepared. Intensities of fluorescence generated in three fluorescence ranges, $\lambda_4=400$ nm, $\lambda_5=440$ nm, $\lambda_6=480$ nm when the solutions are irradiated with an excitation beam of one wavelength of $\lambda=355$ nm are measured (Step 300 in FIG. 5). Four kinds of solutions of Indo-1 and protein having different concentrations are prepared, and intensities of fluorescence generated in the above-described three wavelength ranges when the solutions are irradiated with a one-wavelength excitation beam are measured (Step 310 in FIG. 5). Four kinds of solutions of Indo-1, protein and $Ca^{2+}$ are prepared, and intensities of fluorescence generated in the above-described three fluorescence ranges when the solutions are irradiated with the one-wavelength excitation beam are measured (Step 320 in FIG. 5).

Subsequently 16 sets of initial values of fluorescence coefficients and of equilibrium constants are arbitrary set (Step 330 in FIG. 5). Based on dispersions of measured fluorescence intensity against the fluorescence intensity calculating equations (relationship equations) with the respective sets of initial values, errors are calculated, and it is judged whether there are sets whose errors are in an allowable error range (Step 340 in FIG. 5). If present, one of such sets having a smallest error is judged to be an optimum set of the constants (Step 360 in FIG. 5). If absent, a new set is calculated by the modified simplex method, based on a largest error set, a next largest error set and a smallest error set, and the new set is replaced with a largest error set to generate new 16 sets of the constants (Step 350 in FIG. 5). Subsequently Step 340 follows, and Steps 340 and 350 are repeated until a set with an error within the allowable error range appears.

Figure 4B:
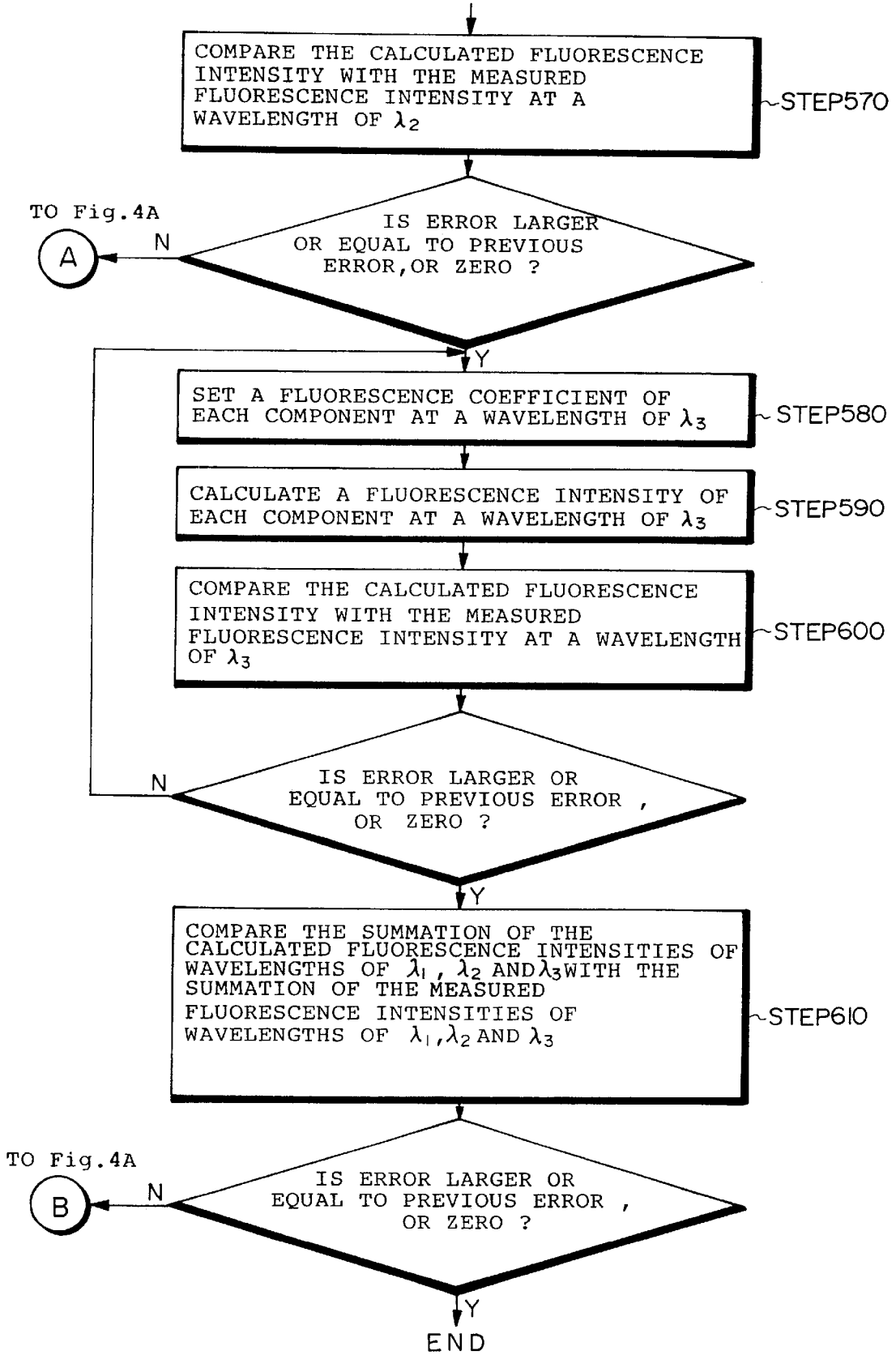

Thus, 15 kinds of constants are optimized to determine respective highly reliable fluorescence coefficients and equilibrium constants (Step 360 in FIG. 5) Note that the detailed procedure of Steps 330–350 are the same as the one of the first embodiment shown in FIGS. 4, 4A and 4B, except wavelengths of $\lambda_4$, $\lambda_5$ and $\lambda_6$ are $\lambda_4$, $\lambda_5$ and $\lambda_6$.

Then, Indo-1 is introduced into a cell (Step 370 in FIG. 5). Intensities of fluorescence generated in the above-described three wavelength ranges when the cell is irradiated with the one-wavelength excitation beam are measured (Step 380 in FIG. 5). The measured fluorescent intensities are substituted into the equilibrium constant equations and the fluorescence intensity calculating equations (relationship equations) to solve these simultaneous equations (Step 390 in FIG. 5) to obtain a $Ca^{2+}$ concentration (Step 400 in FIG. 5).

Thus, an intracellular ion concentration can be measured with high reliability.

Next, the device for measuring an intracellular ion concentration which is used in the method for measuring an intracellular ion concentration according to a third embodiment of the present invention will be explained.

The device for measuring an intracellular ion concentration according to the third embodiment is used in conducting the method for measuring an intracellular ion concentration according to the first embodiment, and will be explained below with reference to FIG. 6. The device according to this embodiment is for the three-wavelengths excitation one-wavelength fluorescence measuring method. A fluorescent probe dye is Fura-2 to measure an intracellular $Ca^{2+}$ concentration. An interfering biosubstance is typically protein. Excitation beams of three wavelengths are 340 nm, 360 nm and 380 nm.

Figure 6:
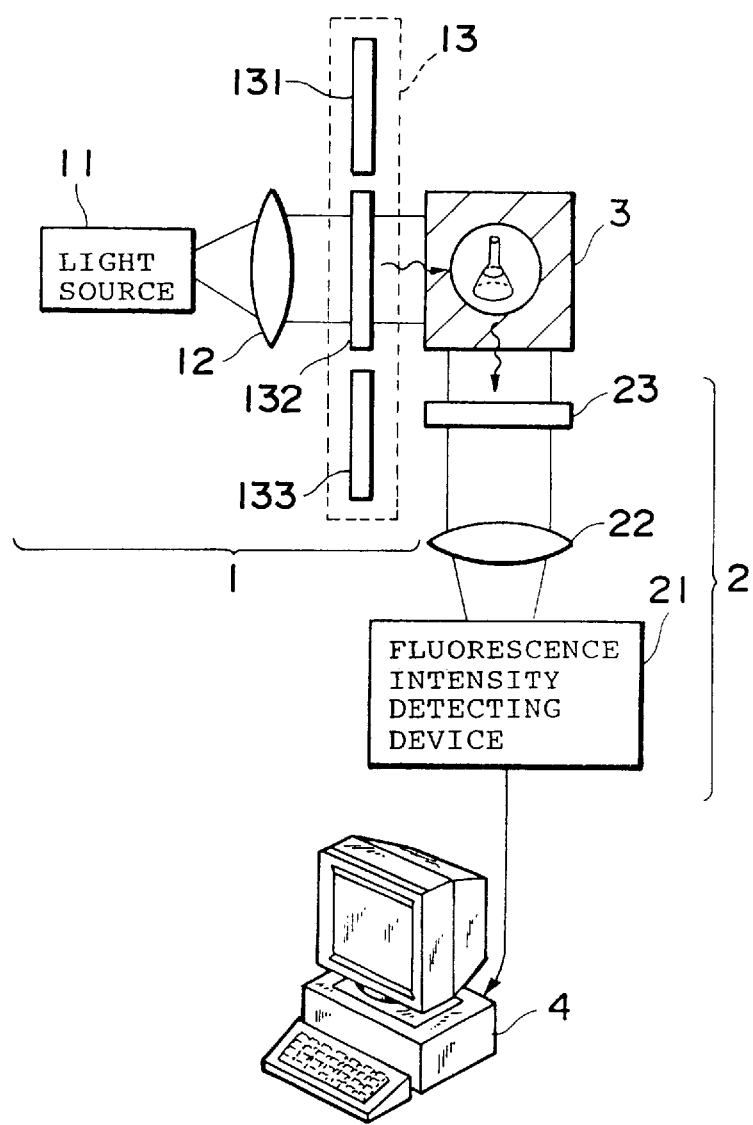
FIG. 6 is a view of the device for measuring an intracellular ion concentration according to a third embodiment of the present invention.

The device shown in FIG. 6 comprises an object-to-be-measured container 3 for holding a specimen (an object to be measured), an excitation beam irradiating unit 1 for irradiating the object to be measured in the container 3 with a required excitation beam, a fluorescence intensity detecting unit 2 for detecting intensities of fluorescence emitted from the object to be measured, first and second processing means for receiving values of the fluorescence intensities from the fluorescence intensity detecting unit 2. The first and the second processing means are incorporated in a processing unit 4. Here, the object to be measured is one of the solutions used in the method according to the first embodiment and a cell with Fura-2 introduced in.

The excitation beam irradiating unit 1 includes a light source 11 for emitting beams of wavelength ranges including three wavelengths of excitation beams, a condenser lens 12 for condensing light from the light source 11, and a filter unit 13 through which an excitation beam of a required wavelength passes. The filter unit 13 includes three filters 131, 132, 133 which can be switched corresponding to required wavelengths of excitation beams. The filters 131, 132, 133 respectively pass beams of wavelengths near 340 nm, 360 nm and 380 nm.

The fluorescence intensity detecting unit 2 includes a condenser lens 22 for condensing light which has passed the filter 23, and a fluorescence intensity detecting device 21 for detecting an intensity of fluorescence detected through the condenser lens 22.

The measuring operation of this device is as follows.

Five solutions of Fura-2 and $Ca^{2+}$ having different concentrations are prepared. One of the solutions is held in the container 3. The filter unit 13 is switched to operate the filter 131. The light source 11 is driven to emit an excitation beam of a wavelength range near 340 nm passing through the filter 131, and the solution in the container 3 is irradiated with this excitation beam. Fluorescence light from the solution irradiated with the excitation beam passes a filter 23 and is inputted to the fluorescence intensity measuring device 21 through the condenser lens 22. The fluorescence intensity detecting device 21 detects an intensity of the input fluorescence and outputs a value of the detected intensity to the processing unit 4. The processing unit 4 stores the value.

Then, the filter unit 13 is switched to pass an excitation beam of a wavelength range near 360 nm through the filter 132 and the solution in the container 3 is irradiated with this beam, and a fluorescence intensity is detected by the fluorescence intensity detecting unit 2. Next, the filter unit 13 is switched to pass an excitation beam of a wavelength range near 380 nm through the filter 133 and the solution is irradiated with this beam, and a fluorescence intensity is detected. Subsequently the same operation is made on the remaining 4 solutions, and intensities of fluorescence generated by excitation beams of the above-described three wavelengths are detected. Next, 4 solutions of Fura-2 and protein having different concentrations are prepared, and in the same way as above, fluorescence intensities are measured when the solutions are irradiated with the excitation beams of the above-described three wavelengths. Then, 4 solutions of Fura-2, protein and $Ca^{2+}$ are prepared, and in the same way as above, fluorescence intensities are measured when the solutions are irradiated with the above-described three wavelengths.

All values of fluorescence intensities of these 13 solutions are stored in the processing unit 4.

Following the fluorescence intensity measure of the 13 solutions, the first processing means incorporated in the, processing unit 4 conducts the following processing.

First, in accordance with the modified simplex method, 16 sets of initial values of the 12 fluorescence coefficients and three equilibrium constants, which have been described in connection with the embodiments of the method are set. Their initial values are selected so that the respective constants which are analytically ones of solutions of cubic equations are not physically insignificant.

Fluorescence intensities calculated based on the 16 sets of initial values are compared with the measured fluorescence intensities, and errors are calculated for each set. If there are sets having an error within an allowable range, one of such sets having the smallest error is judged to be an optimum set of the constants. If all errors exceed the allowable range, a new set is calculated in accordance with the modified simplex method, based on a set having the largest error, a set having the next largest error and a set having the smallest error, and this new set is replaced with the set having the largest error to generate new 16 sets of the constants. The calculated fluorescence intensities of 16 sets are compared with the measured fluorescence intensities, and errors are calculated. If the difference between the largest error and the smallest error is larger than or equal to the previous difference, or zero, a set having a smallest error is judged to be an optimum set. If the difference is smaller than the previous error but not zero, calculating a new set based on a set having the largest error, a set having the next largest error and a set having the smallest error, replacing this new set with the set having the largest error, and comparing the calculated intensities with the measured intensities are successively repeated until the difference between the largest error and the smallest error is larger or equal to the previous error, or zero. Then, the optimum three equilibrium constants and 12 fluorescence coefficients are prepared. The thus-determined three equilibrium constants and 12 fluorescence coefficients are substituted into the equilibrium reaction equations and the fluorescence intensity calculating equations (relationship equations) to be stored in the processing unit 4.

Next, Fura-2 is introduced in a cell, and the cell is placed in the object-to-be-measured container 3. The filter unit 13 is switched to sequentially pass and emit excitation beams of 340 nm, 360 nm and 380 nm to the cell. Intensities of fluorescence generated from the cell are sequentially detected by the fluorescence intensity detecting unit 2. Values of the detected fluorescence intensities are supplied to the processing unit 4, and all values of fluorescence intensities for the excitation beams of the three wavelengths are stored.

The second processing means incorporated in the processing unit 4 substitutes the stored values of fluorescence intensities into the equilibrium reaction equations and the fluorescence intensity calculating equations (relationship equations) to solve their simultaneous equations, and a value of a concentration of $Ca^{2+}$ is given.

Thus, in this device a concentration value of $Ca^{2+}$ is given based on highly reliable fluorescence coefficients and equilibrium constants, and accordingly very reliable.

In the device according to the third embodiment, which is used in the method according to the first embodiment, the filter unit 13 is switched to emit an excitation beam of a required wavelength. But it is also possible that the light source 11 includes three light sources for emitting an excitation beam of respective wavelength, and one of the three light sources is selected corresponding to a required wavelength of the excitation beam to emit the excitation beam of the required wavelength from the selected light source.

Figure 7:
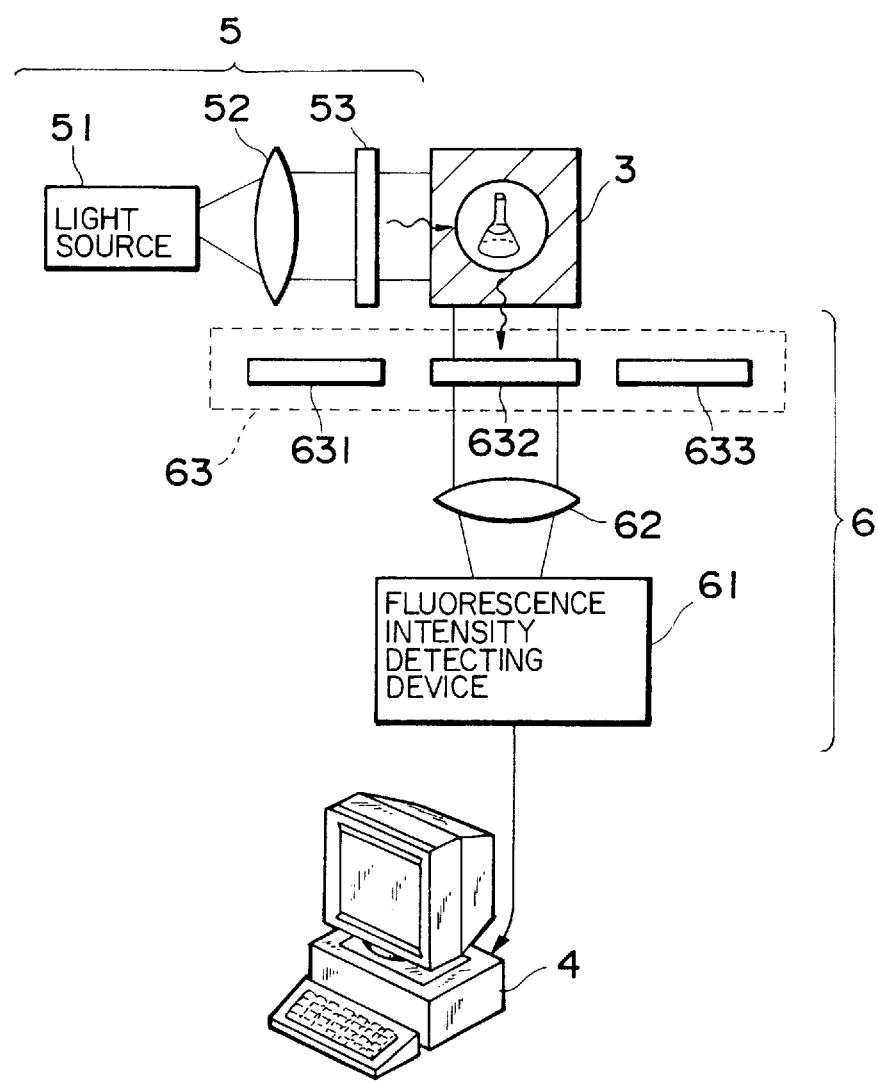
FIG. 7 is a view of the device for measuring an intracellular ion concentration according to a fourth embodiment of the present invention.

Next, the device for measuring an intracellular ion concentration according to a fourth embodiment of the present invention which is used in the method according to the second embodiment of the present invention will be explained, referring to FIG. 7. The device according to this embodiment is used for the one-wavelength excitation three-wavelengths fluorescence intensity measuring method. A fluorescent probe dye is provided by Indo-1 to measure a $Ca^{2+}$ concentration. An interfering biosubstance is typically protein. Three wavelengths of fluorescence to be measured are 400 nm, 440 nm and 480 nm.

The device for measuring an intracellular ion concentration to be used in the method according to the second embodiment comprises an object-to-be-measured container 3 for holding a specimen (an object to be measured): one of the solutions and a cell with Indo-1 introduced in, an excitation beam irradiating unit 5 for irradiating an object to be measured in the container 3 with an excitation beam of a required wavelength, a fluorescence intensity detecting unit 6 for detecting an intensity of fluorescence from the object to be measured, and first and second processing means for receiving, storing and processing values of fluorescence intensities outputted from the fluorescence intensity detecting units. The first and the second processing units are incorporated in a processing unit 4.

The excitation beam irradiating unit 5 includes a light source 51 for emitting beams of wavelength ranges including one wavelength of an excitation beam, and a condenser lens 52 for condensing light from the light source 51, and a filter 53 through which an excitation beam of a required wavelength range passes.

The fluorescence intensity detecting unit 6 includes a filter unit 63 for passing fluorescence of certain wavelength ranges, a condenser lens 62 for condensing light passing the filter 63, and a fluorescence intensity detecting device 61 for receiving light through the condenser lens 62 and detecting a fluorescence intensity. The filter unit 63 includes three filters 631, 632, 633 which respectively pass fluorescence of wavelengths near 400 nm, 440 nm and 480 nm.

The intracellular ion concentration measuring operation of this device is as follows.

First, 5 solutions of Indo-1 and $Ca^{2+}$ having different concentrations are prepared. One of the solutions is placed in the object-to-be-measured container 3. The excitation beam irradiating unit 5 is driven to irradiate the solution in the container 3 with the excitation beam. Then, the filter unit 63 is switched to pass fluorescence of a 400nm-wavelength generated by irradiating the solution with the excitation beam through the filter 631. The fluorescence of 400nm wavelength is applied to the fluorescence intensity detecting device 61 through the condenser lens 62. The fluorescence intensity detecting device 61 detects an intensity of the inputted fluorescence, and output a value of the fluorescence intensity of 400 nm wavelength to the processing unit 4. The processing unit 4 stores this value. Then, the filter unit 63 of the fluorescence intensity detecting unit 6 is switched to pass fluorescence of a wavelength range near 440 nm through the filter 632, and detects an intensity of the fluorescence. Subsequently, the filter unit 63 is switched to pass fluorescence of a wavelength range near 480 nm through the filter 633 and detects an intensity of the fluorescence. Then, this operation is conducted on the remaining 4 solutions, and fluorescence intensities are measured in the three wavelength ranges.

Then, 4 solutions of Indo-1 and protein having different concentrations are prepared. In the same way as above, intensities of fluorescence in the three wavelength ranges are detected. Next, 4 solutions of Indo-1, protein and $Ca^{2+}$ having different concentrations are prepared. In the same way as above, intensities of fluorescence in the three wavelength ranges are detected.

All values of fluorescence intensities detected on the 13 solutions are stored by the processing unit 4.

Following the measurement on the 13 solutions, the same processing as that by the first processing means in the device according to the third embodiment is conducted by the first processing means incorporated in the processing unit 4, and 12 fluorescence constants and 3 equilibrium constants are determined.

Next, Indo-1 is introduced into a cell, and the cell is placed in the object-to-be-measured container 3. The excitation beam irradiating unit 5 is driven to irradiate the cell in the container 3 with the excitation beam. The filter unit 63 is switched to pass fluorescence of the three wavelength ranges generated from the cell by irradiating the cell with the excitation beam, and the fluorescence intensity detecting device 61 detects respective fluorescence intensities in the respective wavelength ranges. Values of the detected fluorescence intensities are applied to the processing unit 4, and the processing unit 4 stores values of fluorescence intensities in all the three wavelength ranges.

The second processing means incorporated in the processing unit 4 substitutes the stored values of fluorescence intensities into the equilibrium reaction equations and the fluorescence intensities calculating equations (relationship equations) to solve their simultaneous equations, and a value of a $Ca^{2+}$ concentration is given.

Thus, in the device according to the fourth embodiment, values of $Ca^{2+}$ are given based on highly reliable fluorescence coefficients and equilibrium constants, and accordingly very reliable.

In the device according to the third embodiment, the light source 51 emits beams of a wavelength range including one required wavelength, but a light source which emits an excitation beam of the one required wavelength may be used.

In the devices for measuring an intracellular ion concentration according to the third and the fourth embodiments, the fluorescence intensity detecting devices may be provided by spectrofluorescence meters. A fluorescence coefficient changes depending on a thickness of a specimen of an object-to-be-measured, i.e., an optical path length, and it is necessary to unify optical path lengths of objects to be measured. In the spectrofluorescence meters of the third and the fourth embodiments, a thickness of a cell to be measured is an optical path length, and a value of the optical path length can be always constant. The fluorescence intensity detecting device can be provided by fluorescence microscopes with photometers. For the measurement by these fluorescence microscopes it is necessary to incorporate cone focal optical systems which can provide sectional images of a certain thickness.

By the method and the device for measuring an intracellular ion concentration according to the present invention, a concentration of ions to be measured, $Mg^{2+}$ can be given. For this measurement a fluorescent probe dye may be one that is suitable to measure a concentration of $Mg^{2+}$.

Fluorescent probe dyes, and excitation wavelengths are not essentially limited to those used in the embodiments. Even when excitation wavelengths are changed depending on characteristics of flourescent dyes, the object of the present invention can be still attained.

The method and the device for measuring an intracellular ion concentration of the present invention can be applied to intracellular ions and fluorescence probe dyes incorporated in U.S. Pat. No. 5,319,209, and the U.S. Pat. No. 5,319,209 is hereby incorporated by reference.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

What is claimed is:

1. A device for measuring an intracellular ion concentration $X_I$, where the ion is selected from the group consisting of $Ca^{+2}$, $Mg^{+2}$, $H^+$ and $Na^+$, in a cell containing said ion in which a fluorescent probe dye has been introduced, whereby a concentration of said ion in the cell is measured based on intensities of fluorescence generated by irradiating the cell with excitation beams, said device comprising:

A) container means for holding an object to be measured, said object to be measured being at least one of (1)–(4)
   (1) at least one living cell containing (a) intercellular ions to be quantitatively measured, (b) a fluorescent probe dye which has been introduced into said cell, and (c) at least one interfering biosubstance found in said cell which is different from said free ions, and which interacts with said fluorescent probe dye and either (i) changes the fluorescence intensity or fluorescence spectrum of said fluorescent probe dye, or (ii) affects an equilibrium constant $K_{FI}$ between the fluorescent probe dye, the intracellular ion and their complex;
   (2) at least one first mixed solution containing (a) said intracellular ions and (b) said fluorescent probe dye;
   (3) at least one second mixed solution containing (b) said fluorescent probe dye and (c) said interfering biosubstance; and
   (4) at least one third mixed solution containing (a) said intracellular ions, (b) said fluorescent probe dye, and (c) said interfering biosubstance;

B) excitation beam irradiating means which generates excitation beams of at least three different wavelengths and irradiating the object to be measured in said container with the beams so generated;

C) fluorescence intensity detecting means for measuring the intensities of fluorescence generated by the object to be measured in said container when irradiated by said excitation beams;

D) first processing means for receiving output signals of the fluorescence intensity detecting means, storing the output signals, and in accordance with a successive approximation, using the output signals stored, optimizing three equilibrium constants: $K_{FI}$, $K_{PF}$ and $K_{PFI}$ in the following three kinds of independent equilibrium constant equations of the fluorescent probe dye, the ions to be measured, the interfering biosubstance and their complexes in the cell, and 12 kinds of fluorescence coefficients: $I_{\lambda 1,F}$, $I_{\lambda 2,F}$, $I_{\lambda 3,F}$, $I_{\lambda 1,PF}$, $I_{\lambda 2,PF}$, $I_{\lambda 3,PF}$, $I_{\lambda 1,FI}$, $I_{\lambda 2,FI}$, $I_{\lambda 3,FI}$, $I_{\lambda 1,PFI}$, $I_{\lambda 2,PFI}$, and $I_{\lambda 3,PFI}$ in the following relationship equations between the intensities of the fluorescence, and the concentrations of fluorescent probe dye, ions to be measured, interfering biosubstance, and their complexes by
   (1) setting initial values of the three equilibrium constants, and initial values of the 12 kinds of fluorescence coefficients,
   (2) calculating and comparing errors between fluorescence intensities calculated based on the initial values, and fluorescence intensities measured,
   (3) if the error is within an allowable range, the three equilibrium constants and the 12 kinds of fluorescence coefficients are deemed optimized, if the error exceeds the allowable range, setting new values of the three equilibrium constants and the 12 kinds of fluorescence coefficients,
   (4) calculating errors between calculated fluorescence intensities, and fluorescence intensities measured,
   (5) comparing the error based on the newly set values with the previous error, and
   (6) if the error is larger or equal to the previous error, or zero, the three equilibrium constants and the 12 kinds of fluorescence coefficients are deemed optimized, if the error is less than the previous error but not zero, successively repeating setting new values of the three equilibrium constants and the 12 kinds of fluorescence coefficients, calculating errors between calculated fluorescence intensities, and fluorescence intensities measured and comparing the error with the previous error until the error is larger or equal to the previous error, or zero; and E) second processing means for determining a concentration of the ions to be measured in the cell by solving simultaneous equations of (1) equilibrium constant equations of the fluorescence probe dye, interfering biosubstance, the ions to be measured and their complexes in the cell, and (2) relationship equations between the intensities of the fluorescence generated by the excitation beams at the respective wavelengths, and the concentrations of fluorescence probe dye, interfering biosubstance, the ions to be measured and their complexes, wherein the equations are $$K_{FI} = X_F \cdot X_I / X_{FI}$$

$$K_{PF} = X_P \cdot X_F / X_{PF}$$

$$K_{PFI} = X_P \cdot X_{FI} / X_{PFI} \text{ (or, } K_{PFI} = X_{PF} \cdot X_I / X_{PFI}$$

$$I_{\lambda 1} = I_{\lambda 1,F} \cdot X_F + I_{\lambda 1,PF} \cdot X_{PF} + I_{\lambda 1,FI} \cdot X_{FI} + I_{\lambda 1,PFI} \cdot X_{PFI}$$

$$I_{\lambda 2} = I_{\lambda 2,F} \cdot X_F + I_{\lambda 2,PF} \cdot X_{PF} + I_{\lambda 2,FI} \cdot X_{FI} + I_{\lambda 2,PFI} \cdot X_{PFI}$$

$$I_{\lambda 3} = I_{\lambda 3,F} \cdot X_F + I_{\lambda 3,PF} \cdot X_{PF} + I_{\lambda 3,FI} \cdot X_{FI} + I_{\lambda 3,PFI} \cdot X_{PFI}$$

wherein $X_F$: a concentration of a fluorescence probe dye (F)

$X_I$: a concentration of ions to be measured (I)

$X_P$: a concentration of interfering biosubstance (P)

$X_{FI}$: a concentration of fluorescence probe dye-ions to be measured complex (FI)

$X_{PF}$: a concentration of interfering biosubstance-fluorescence probe dye complex (PF)

$X_{PFI}$: a concentration of interfering biosubstance-fluorescence probe dye-ions to be measured complex (PFI)

$K_{FI}$: an equilibrium constant between fluorescence probe dye, ions to be measured and the FI complex $K_{PF}$: an equilibrium constant between interfering biosubstance, fluorescence probe dye and the PF complex $K_{PFI}$: an equilibrium constant among interfering biosubstance, fluorescence probe dye, ions to be measured and the PFI complex $I_{\lambda i}$: a measured fluorescence intensity for an excitation beam of wavelength $\lambda_i$ $I_{\lambda i,F}$: a fluorescence intensity coefficient of a fluorescence probe dye for an excitation beam of wavelength $\lambda_i$ $I_{\lambda i,PF}$: a fluorescence intensity coefficient of interfering biosubstance-fluorescence probe dye complex for an excitation beam of wavelength $\lambda_i$ $I_{\lambda i,FI}$: A fluorescence intensity coefficient of fluorescence probe dye-ions to be measured complex for an excitation beam at wavelength $\lambda_i$ $I_{\lambda i,PFI}$: a fluorescence intensity coefficient of interfering biosubstance-fluorescence probe dye-ions to be measured complex for excitation beam of a wavelength $\lambda_i$ i: 1, 2, or 3.

2. A device for measuring an intracellular ion concentration according to claim 1, wherein the excitation beam irradiating means comprises one light source for emitting beams of a wavelength range including three wavelengths of the excitation beams to be used, and three filters through which a beam of a wavelength range near the respective wavelength of the excitation beam passes, one of the three filters being selected in accordance with a predetermined wavelength of the excitation beam, the beam of the predetermined wavelength near the wavelength of the excitation beam passing through the selected filter.

3. A device for measuring an, intracellular ion concentration according to claim 1, wherein the excitation beam irradiating means comprises three light sources for emitting an excitation beam of a different wavelength, one of the light sources being selected in accordance with a predetermined wavelength of the excitation beam, the excitation beam of the predetermined wavelength being emitted from the selected light source.

4. A device for measuring an intracellular ion concentration according to claim 1, wherein 16 sets of the values of the three kinds of equilibrium constants and the 12 fluorescence coefficients are set in the first processing means in accordance with the modified simplex method.

5. A device for measuring an intracellular ion concentration according to claim 1, wherein the ions to be measured are $Ca^{2+}$, and the fluorescence probe dye in Fura-2.

6. A device for measuring an intracellular ion concentration according to claim 1, wherein the ions to be measured are $Na^+$, and the fluorescence probe dye is Sodium-binding benzofuran isophthalate.

7. A device for measuring an intracellular ion concentration according to claim 1, wherein the ions to be measured are $H^+$, and fluorescence probe dye is 2',7'-bis-(2-carboxyethyl)-(5-(and-6)-carboxyfluoresoein).

8. A device for measuring an intracellular ion concentration according to claim 1, wherein the ions to be measured are $H^+$, and the fluorescence probe dye is carboxy-seminaphthorhodafluor-6.

9. A device for measuring an intracellular ion concentration according to claim 1, wherein the ions to be measured are $Mg^{2+}$, and the fluorescence probe dye is Mag-Fura-2.

10. A device for measuring an intracellular ion concentration according to claim 1, wherein the interfering biosubstance is bioprotein.

11. A device for measuring an intracellular ion concentration $X_I$, where the ion is selected from the group consisting of $Ca^{+2}$, $Mg^{+2}$, $H^+$ and $Na^+$, in a cell containing said ion in which a fluorescent probe dye has been introduced, whereby a concentration of said ion in the cell is measured based on intensities of fluorescence generated by irradiating the cell with excitation beams, said device comprising:

A) container means for holding an object to be measured, said object to be measured being at least one of (1)–(4)

(1) at least one living cell containing (a) intercellular ions to be quantitatively measured, (b) a fluorescent probe dye which has been introduced into said cell, and (c) at least one interfering biosubstance found in said cell which is different from said free ions, and which interacts with said fluorescent probe dye and either (i) changes the fluorescence intensity or fluorescence spectrum of said fluorescent probe dye, or (ii) affects an equilibrium constant $K_{FI}$ between the fluorescent probe dye, the intracellular ion and their complex;

(2) at least one first mixed solution containing (a) said intracellular ions and (b) said fluorescent probe dye;

(3) at least one second mixed solution containing (b) said fluorescent probe dye and (c) said interfering biosubstance; and (4) at least one third mixed solution containing (a) said intracellular ions, (b) said fluorescent probe dye, and (c) said interfering biosubstance;

B) excitation beam irradiating means which generates an excitation beam of a single wavelengths and irradiating the object to be measured in said container with the beam so generated;

C) fluorescence intensity detecting means for measuring the intensities of fluorescence at at least three wave lengths generated by the object to be measured in said container when irradiated by said excitation beam;

D) first processing means for receiving output signals of the fluorescence intensity detecting means, storing the output signals, and in accordance with a successive approximation, using the output signals stored, optimizing three equilibrium constants: $K_{FI}$, $K_{PF}$ and $K_{PFI}$ in the following three kinds of independent equilibrium constant equations of the fluorescent probe dye, the ions to be measured, the interfering biosubstance and their complexes in the cell, and 12 kinds of fluorescence coefficients: $I_{\lambda 1,F}$, $I_{\lambda 2,F}$, $I_{\lambda 3,F}$, $I_{\lambda 1,PF}$, $I_{\lambda 2,PF}$, $I_{\lambda 3,PF}$, $I_{\lambda 1,FI}$, $I_{\lambda 2,FI}$, $I_{\lambda 3,FI}$, $I_{\lambda 1,PFI}$, $I_{\lambda 2,PFI}$, and $I_{\lambda 3,PFI}$, in the following relationship equations between the intensities of the fluorescence, and the concentrations of fluorescent probe dye, ions to be measured, interfering biosubstance, and their complexes by (1) setting initial values of the three equilibrium constants, and initial values of the 12 kinds of fluorescence coefficients, (2) calculating and comparing errors between fluorescence intensities calculated based on the initial values, and fluorescence intensities measured, (3) if the error is within an allowable range, the three equilibrium constants and the 12 kinds of fluorescence coefficients are deemed optimized, if the error exceeds the allowable range, setting new values of the three equilibrium constants and the 12 kinds of fluorescence coefficients, (4) calculating errors between calculated fluorescence intensities, and fluorescence intensities measured, (5) comparing the error based on the newly set values with the previous error, and (6) if the error is larger or equal to the previous error, or zero, the three equilibrium constants and the 12 kinds of fluorescence coefficients are deemed optimized, if the error is less than the previous error but not zero, successively repeating setting new values of the three equilibrium constants and the 12 kinds of fluorescence coefficients, calculating errors between calculated fluorescence intensities, and fluorescence intensities measured and comparing the error with the previous error until the error is larger or equal to the previous error, or zero; and E) second processing means for determining a concentration of the ions to be measured in the cell by solving simultaneous equations of (1) equilibrium constant equations of the fluorescence probe dye, interfering biosubstance, the ions to be measured and their complexes in the cell, and (2) relationship equations between the intensities of the fluorescence generated by the excitation beams at the respective wavelengths, and the concentrations of fluorescence probe dye, interfering biosubstance, the ions to be measured and their complexes, wherein the equations are $K_{FI} = X_F \cdot X_I / X_{FI}$ $K_{PF} = X_P \cdot X_F / X_{PF}$ $K_{PFI} = X_P \cdot X_{FI} / X_{PFI}$ (or, $K_{PFI} = X_{PF} \cdot X_I / X_{PFI}$)

$I_{\lambda 1} = I_{\lambda 1,F} \cdot X_F + I_{\lambda 1,PF} \cdot X_{PF} + I_{\lambda 1,FI} \cdot X_{FI} + I_{\lambda 1,PFI} \cdot X_{PFI}$ $I_{\lambda 2} = I_{\lambda 2,F} \cdot X_F + I_{\lambda 2,PF} \cdot X_{PF} + I_{\lambda 2,FI} \cdot X_{FI} + I_{\lambda 2,PFI} \cdot X_{PFI}$ $I_{\lambda 3} = I_{\lambda 3,F} \cdot X_F + I_{\lambda 3,PF} \cdot X_{PF} + I_{\lambda 3,FI} \cdot X_{FI} + I_{\lambda 3,PFI} \cdot X_{PFI}$ wherein $X_F$: a concentration of a fluorescence probe dye (F)

$X_I$: a concentration of ions to be measured (I)

$X_P$: a concentration of interfering biosubstance (P)

$X_{FI}$: a concentration of fluorescence probe dye-ions to be measured complex (FI)

$X_{PF}$: a concentration of interfering biosubstance-fluorescence probe dye complex (PF)

$X_{PFI}$: a concentration of interfering biosubstance-fluorescence probe dye-ions to be measured complex (PFI)

$K_{FI}$: an equilibrium constant between fluorescence probe dye, ions to be measured and the FI complex $K_{PF}$: an equilibrium constant between interfering biosubstance, fluorescence probe dye and the PF complex $K_{PFI}$: an equilibrium constant among interfering biosubstance, fluorescence probe dye, ions to be measured and the PFI complex $I_{\lambda i}$: a measured fluorescence intensity for an excitation beam of wavelength $\lambda_i$ $I_{\lambda i,F}$: a fluorescence intensity coefficient of a fluorescence probe dye for an excitation beam of wavelength $\lambda_i$ $I_{\lambda i,PF}$: a fluorescence intensity coefficient of interfering biosubstance-fluorescence probe dye complex for an excitation beam of wavelength $\lambda_i$ $I_{\lambda i,FI}$: A fluorescence intensity coefficient of fluorescence probe dye-ions to be measured complex for an excitation beam at wavelength $\lambda_i$ $I_{\lambda i,PFI}$: a fluorescence intensity coefficient of interfering biosubstance-fluorescence probe dye-ions to be measured complex for excitation beam of a wavelength $\lambda_i$ i: 1, 2, or 3.

12. A device for measuring an intracellular ion concentration according to claim 11, wherein the excitation beam irradiating means comprises one light source for emitting beams of a wavelength range including one wavelength of the excitation beam to be used, and one filter through which a beam of a wavelength range near the wavelength of the excitation beam to be used passes.

13. A device for measuring an intracellular ion concentration according to claim 11, wherein the excitation light irradiating means includes a light source for emitting the excitation beam of one wavelength.

14. A device for measuring an intracellular ion concentration according to claim 11, wherein the fluorescence intensity detecting means comprises three filters through which fluorescence light of different wavelength ranges passes, one of the three filters being selected in accordance with a predetermined fluorescence wavelength range, and fluorescence of the predetermined fluorescence wavelength range passing through the selected filter.

15. A device for measuring an intracellular ion concentration according to claim 11, wherein the successive approximation is carried out by a modified simplex method.

16. A device for measuring an intracellular ion concentration according to claim 11, wherein 16 sets of the values of the three kinds of equilibrium constants and 16 sets of the values of the 12 fluorescence coefficients are set in the first processing means in accordance with the modified simplex method.

17. A device for measuring an intracellular ion concentration according to claim 11, wherein the ions to be measured are $Ca^{2+}$, and the fluorescence probe dye is Indo-1.

18. A device for measuring an intracellular ion concentration according to claim 11, wherein the ions to be measured are $Na_+$, and the fluorescence probe dye is FCryp-2.

19. A device for measuring an intracellular ion concentration according to claim 11, wherein the ions to be measured are $H_+$, and the fluorescence probe dye is Carboxyseminaphthorhodafluor-1.

20. A device for measuring an intracellular ion concentration according to claim 11, wherein the ions to be measured are $H_+$, and the fluorescence probe dye is Carboxyseminaphthorhodafluor-2.

21. A device for measuring an intracellular ion concentration according to claim 11, wherein the ions to be measured are $H^+$, and the fluorescence probe dye is Carboxyseminaphthorhodafluor-6.

22. A method for measuring an intracellular ion concentration according to claim 11, wherein the ions to be measured are $H^+$, and the fluorescence probe dye is Carboxyseminaphthorhodaflour-X.

23. A device for measuring an intracellular ion concentration according to claim 11, wherein the ions to be measured are $Mag^{2+}$, and the fluorescence probe dye is Mag-indo-1.

24. A device for measuring an intracellular ion concentration according to claim 11, wherein the interfering biosubstance is protein.

* * * * *